(12) United States Patent
Wan et al.

(10) Patent No.: US 6,458,156 B1
(45) Date of Patent: Oct. 1, 2002

(54) EXPANSIBLE BIOPROSTHETIC VALVE STENT

(75) Inventors: Wan-Kei Wan, London (CA); Anthony Duncan, London (CA); Gordon Campbell, London (CA); Derek Boughner, London (CA)

(73) Assignee: The University of Western Ontario, London (CA)

( * ) Notice: Subject to any disclaimer, the term of this patent is extended or adjusted under 35 U.S.C. 154(b) by 0 days.

(21) Appl. No.: 09/194,634

(22) PCT Filed: May 30, 1997

(86) PCT No.: PCT/CA97/00374

§ 371 (c)(1),
(2), (4) Date: Sep. 8, 1999

(87) PCT Pub. No.: WO97/46177

PCT Pub. Date: Dec. 11, 1997

Related U.S. Application Data (60) Provisional application No. 60/018,846, filed on May 31, 1996.

(51) Int. Cl.$^7$ .................................................. A61F 2/24
(52) U.S. Cl. ..................................................... 623/2.14
(58) Field of Search .................................. 623/2.1, 2.11, 623/2.12, 2.13, 2.14, 2.15, 2.16, 2.17, 2.18, 2.19, 1.49, 1.44, 1.45, 1.46, 1.38; 128/898

(56) References Cited

U.S. PATENT DOCUMENTS

| | | | | |
|---|---|---|---|---|
| 3,673,612 A | | 7/1972 | Merrill et al. | |
| 4,664,857 A | | 5/1987 | Nambu | |
| 4,734,097 A | * | 3/1988 | Tanabe et al. | 623/11 |
| 4,808,353 A | | 2/1989 | Nambu et al. | |
| 4,871,357 A | * | 10/1989 | Hsu et al. | 604/26 |
| 4,916,193 A | * | 4/1990 | Tang et al. | 525/413 |
| 5,275,838 A | | 1/1994 | Merrill | |
| 5,545,213 A | * | 8/1996 | Keogh et al. | 623/1 |
| 5,549,665 A | | 8/1996 | Vesely et al. | |
| 5,804,318 A | * | 9/1998 | Pinchuk et al. | 428/421 |
| 5,824,049 A | * | 10/1998 | Ragheb et al. | 623/1 |
| 6,028,164 A | * | 2/2000 | Loomis | 528/354 |
| 6,031,059 A | * | 2/2000 | Vanderlaan et al. | 526/279 |
| 6,096,018 A | * | 8/2000 | Luzio et al. | 604/500 |
| 6,132,473 A | * | 10/2000 | Williams et al. | 623/66.1 |

* cited by examiner

Primary Examiner—Corrine McDermott
Assistant Examiner—Hien Phan
(74) Attorney, Agent, or Firm—Dinsmore & Shohl LLP (57) ABSTRACT

A bioprosthetic valve stent is fabricated from a hydrogel, and a bioprosthetic heart valve comprises such a stent. A method for fabricating a hydrogel bioprosthetic valve stent comprises filling a mold cavity with a solution of a hydrogel, allowing the hydrogel to solidity, removing the solidified hydrogel from the mold cavity and hydrating the hydrogel.

15 Claims, 4 Drawing Sheets

TOP

BASE

MOLD CENTER

FIG. 5

EXPANSIBLE BIOPROSTHETIC VALVE STENT

This application claims the benefit of Ser. No. 60/018,846 filed May 31, 1996.

FIELD OF THE INVENTION

This invention relates to bioprosthetic valves and more particularly to a method of fabricating expansible bioprosthetic valve stents.

BACKGROUND OF THE INVENTION

Two basic types of artificial heart valves are available for replacement of diseased human heart valves. The first type, mechanical valves, are constructed of synthetic rigid materials such as plastic or metal. Their use is associated with thrombogenesis, requiring valve recipients to be on long term anti-coagulation.

The second type, tissue valves or bioprosthetic valves, consist of valve leaflets of preserved animal tissue mounted on an artificial support or "stent".

The durability of bioprosthetic heart valves is limited to about 12 to 15 years. The limitations in the long term performance of bioprosthetic heart valves are believed to be due largely to the mechanical properties of the valve and the stresses imposed on the tissue leaflets by the rigidity of the stent structure while the aortic root to which the artificial valve is attached expands and contracts during the cardiac cycle. An important feature of the natural heart valve is its ability to expand in diameter by more than 10% during systole. This ability of the aortic root to expand facilitates blood flow due to a better opening of the valve during systole and contributes to minimal bending of the cusps, thus reducing possible internal flexural fatigue.

In an attempt to overcome the rigidity of artificial heart valves and accommodate the expansion of the aortic root during systole, a bioprosthetic heart valve with pivoting stent posts has been devised (Canadian Patent No. 2,123,824).

U.S. Pat. No. 5,258,023 discloses a prosthetic heart valve in which the valve leaflets are fashioned from synthetic materials, in an attempt to avoid the mechanical failure of natural tissue leaflet material.

Although these designs allowed for improved hemodynamics, they did not totally solve the problems arising from the rigidity of artificial heart valve stents. There remained a need for an artificial heart valve stent that is expansible, resilient and tough and which provides a better opening of the valve during systole to facilitate blood flow and contributes to minimal bending of the cusps to reduce valve failure.

SUMMARY OF THE INVENTION

The present invention provides a bioprosthetic stent fabricated from a hydrogel. A hydrogel stent combines sufficient strength for use in a bioprosthetic valve with pliability and elasticity characteristics which much more closely resemble those of the aortic root than previously available valve stents.

The invention provides a bioprosthetic valve stent fabricated from a hydrogel, wherein the hydrogel, when hydrated, has (a) a strain value at ultimate tensile stress (UTS) greater than the maximum strain occurring in a human aortic root under physiological conditions;

(b) an elastic modulus similar to that of the aortic root; and (c) a relaxation rate similar to that of the aortic root.

The invention provides a method of fabricating a bioprosthetic valve stent comprising the steps of (a) preparing a mold cavity corresponding in shape to the stent to be fabricated;

(b) filling said mold cavity with a solution of a selected hydrogel;

(c) allowing the hydrogel to solidify; and (d) removing the solid hydrogel from the mould cavity and hydrating the solidified hydrogel for a suitable period of time.

The invention provides a bioprosthetic heart valve comprising (a) a stent in accordance with any of claims 1 to 5, (b) leaflet valve means having three generally triangular leaflets defining respective cusps which are adapted to open and close during heart systole and diastole respectively; and (c) means for attaching the leaflet valve means to the stent.

BRIEF DESCRIPTION OF THE DRAWINGS

Certain embodiments of the invention are described, reference being made to the accompanying drawings, wherein.

DETAILED DESCRIPTION OF THE INVENTION

The present invention provides an expansible bioprosthetic valve stent fabricated from a hydrogel and a method of making such a stent. The stent of the invention is resilient and expansible and, at the same time, tough.

Hydrogels are hydrophilic macromolecular or polymer networks that are capable of imbibing large amounts of water without dissolving. The networks contain crosslinks, crystalline regions and entanglements between the polymer molecules.

Hydrogels have the interesting properties of being hard and stiff when in the dry state but soft and pliable when hydrated. These properties make hydrogels ideal materials for fabrication of bioprosthetic valve stents, in that they can be milled or machined into any desired shape when dry and hard, but become pliable and expansible when hydrated.

Hydrogels are soluble in various non-aqueous solvents and may therefore also be fashioned into valve stents by casting in suitable moulds.

In accordance with a preferred embodiment, the invention comprises a heart valve stent fabricated from a hydrogel.

The heart valve stent maybe for a mitral valve, an aortic valve or tricuspid valve. It is also contemplated that the bioprosthetic valve of the present invention may be used to replace valves of the human body other than heart valves. For example, in an alternative embodiment, the valve of the invention maybe modified for use in the urinary tract to replace a defective sphincter muscle in order to treat incontinence. Also, the valve of the invention may be used in the eye or in the brain to reduce fluid pressure.

In accordance with a preferred embodiment, the invention comprises an aortic valve stent fabricated from a hydrogel.

Any hydrogel that is biocompatible and has mechanical characteristics that mimic those of the aortic root (eg. compliance and toughness), would be suitable for fabrication of the expansible heart valve stent of the present invention.

A valve stent in accordance with the invention may, for example, be fabricated from a neutral hydrogel such as poly(vinyl alcohol), polyacrylamide, poly(N-vinylpyrolidone), poly(hydroxyethyl methacrylate), poly(ethylene oxide), poly(ethylene glycol), poly(ethylene glycol) monomethyl ether, cellulose ( or other polysaccharides)or from an ionic hydrogel such as poly(acrylate), polymethacrylate, poly(methylacrylate), poly(methyl methacrylate) and poly(lactic acid).

It is desirable that a hydrogel for a bioprosthetic valve stent for an artificial aortic valve should have the following characteristics when fully hydrated:

1. a strain at ultimate tensile strength (UTS) value above the maximum strain of the aortic root under physiological conditions, to ensure that the stent will expand to the dimensions reached by the aortic root during systole.

The elastic region of the stent material, ie. the stress region within which deformation is reversible, should not be exceeded by the stretch induced by expansion of the aorta within the physiological blood pressure range and plastic deformation of the hydrogel material of the stent should not occur. "Physiological blood pressure range" means the blood pressure range encountered in the human body, either in normal or diseased states.

2. a compliance or elastic modulus similar to that of the aortic root;

3. a relaxation rate similar to that of the aortic root.

A hydrogel for use in a heart valve stent should have a strain at UTS of at least about 20%. A strain at UTS in the range of about 30% to about 90% is preferred.

The hydrogel should have a modulus in the range of about 0.01 to about 10 Mpa; a range of about 0.5 to about 2 is preferred and a range of about 0.1 to 1 is especially preferred.

The hydrogen should have a relaxation rate of about 3 to about 9 kPa/sec; a range of about 4 to about 8 is preferred and a range of about 5 to about 7 is especially preferred.

In accordance with a preferred embodiment, an aortic valve stent in accordance with the invention is fabricated from a hydrogel having a strain at UTS in the range of about 30% to about 90%, an elastic modulus in the range of about 0.1 to about 1 Mpa and a relaxation time in the range of about 5 to about 7 kPa/sec.

Maximum systolic pressures encountered in vivo in humans (120 mm Hg for a human at rest to 400 mm Hg during intense physical exercise) yield a computed theoretical stress in the range of 0.32 to 1.00 Mpa, using the Laplace or "Hoop Stress" equation: stress=pressure×radius÷thickness of aortic root.

A hydrogel heart valve stent is able to mimic natural radial heart valve expansion at the pressures encountered during the cardiac cycle in humans. It is therefore able to reproduce more closely the natural function of the valve which it replaces.

Any valve stent design may be selected for fabrication in hydrogel. In accordance with one embodiment, the stent may be machined to the required dimensions starting from a block or cylinder of dehydrated hydrogel. The machining process may be controlled by computer aided machining. For Example, this has been done using a three-axis digital milling machine fitted with a manually rotated vertical indexing head. In the machining process, a poly(hema) blank of 1.75"×1.25" was used. It was kept cool during machining using compressed air. The finished stent was transferred into water for rehydration (4–6 hours). Upon rehydration of the machined heart valve stent, it becomes expansible.

In accordance with a further embodiment, solution casting provides a convenient method of fabricating valve stents from a hydrogel, as described in Example 4. A suitable mould cavity is formed around a stent of the desired design and the mould cavity is used to cast stents from a selected hydrogel which is dissolved in a suitable solvent and poured into the mould.

The stent used to form the mould cavity may be of any material; for example, it may be a hydrogel stent prepared by machining of a block of hydrogel or may be of plastic or other rigid material.

A solution of a selected hydrogel is poured into the mould and allowed to solidify, the mould is opened and the formed hydrogel stent is placed in water to hydrate. The hydrogel stent is up to 90% hydrated within 3 to 6 hours but hydration for 24 hours can be carried out to ensure full hydration. The completeness of hydration can be monitored by weighing the dry stent, followed by weighing at intervals during hydration until a constant weight is achieved.

In accordance with a preferred embodiment, a stent is made by solution casting from PVA. The PVA stent is subjected to one freeze-thaw cycle while still in the mould, to give it sufficient rigidity for removal from the mould. After removal from the mould, the PVA stent is subjected to further freeze-thaw cycles until the desired aorta-mimicing mechanical characteristics are achieved. Alternatively, the stent can be left in the mould after the first freeze-thaw cycle and subjected to further freeze-thaw cycles in the mould until the desired mechanical characteristics are achieved. The stent is then removed from the mould. In a preferred embodiment, a total of four freeze-thaw cycles are used. In one embodiment, each freeze-thaw temperature cycle employs a freezing temperature in the range of about −70° C. to −30° C. and a thaw temperature in the range of about 15° C. to 30° C.

A hydrogel stent in accordance with the invention is inserted into a conventional Dacron cover, as is done with a rigid stent. The cover is then attached to valve leaflets in a conventional manner, as described for example in Canadian Patent 2,123,824.

For example, leaflets may comprise glutaraldehyde-pretreated bovine pericardial tissue or glutaraldehyde-pretreated porcine aortic valve cusps.

EXAMPLES

The examples are described for the purposes of illustration and are not intended to limit the scope of the invention.

Example 1

Poly(hema) (# 19,206.6) was obtained from Aldrich Chemical. A 13% poly(hema) solution in methanol was prepared, cast as a film onto a Teflon surface and freeze-dried overnight. The sample was then rehydrated in distilled water for 24 hours and cut into 5 mm×10 mm strips. Standard uniaxial mechanical testing was performed using a MTS tensile tester (MTS Corp., Minneapolis, Minn.) and comparing the sample with a polypropylene sample.

The results are shown in Table 1 and demonstrate that poly(hema) has high extensibility, high compliance and an ability to withstand pressures higher than those encountered physiologically.

Example 2

Figure 1A:
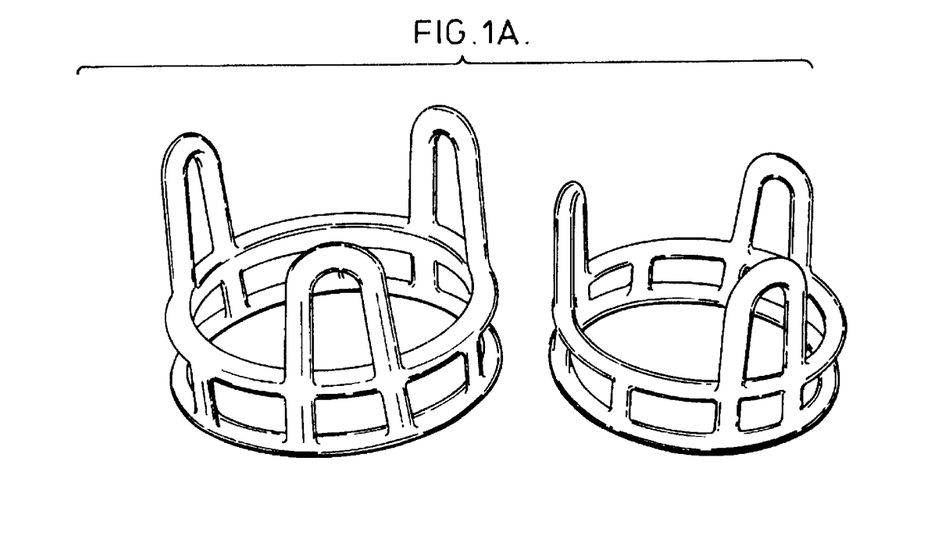
FIG. 1A shows a hydrated poly(hema) heart valve stent (left) and an acrylic stent (right), in uncompressed state.
Figure 1B:
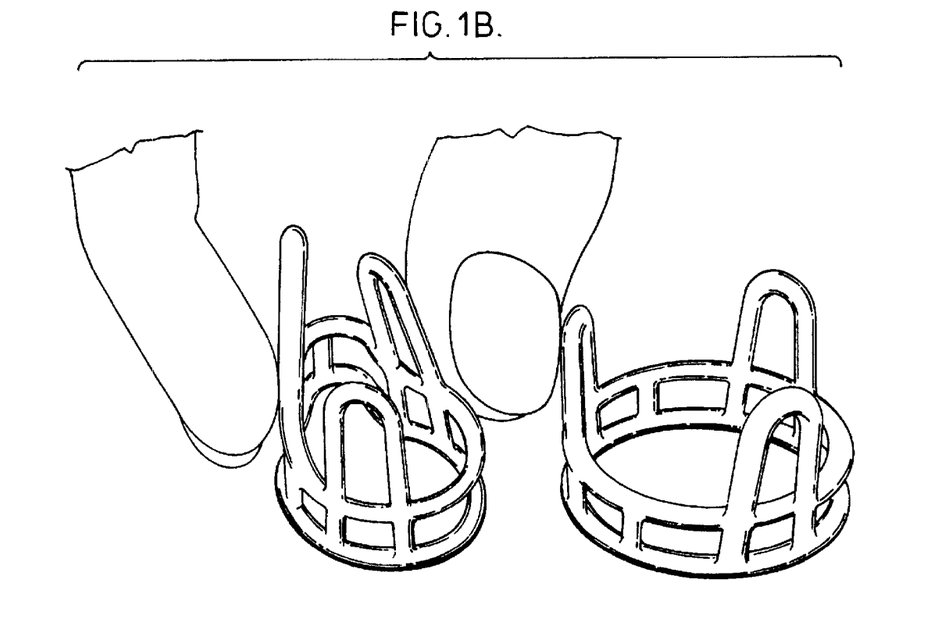
FIG. 1B shows a hydrated poly(hema) stent (left) in compressed state and an acrylic stent (right) in uncompressed state.

A heart valve stent was fabricated using poly(hema) and a well developed CAD/CNC milling apparatus. Total milling time was about 2 hours. FIG. 1 shows one such stent in both uncompressed and compressed states. The compressed state illustrates the expansibility of a poly(hema) heart valve stent.

Example 3

The mechanical properties of PVA were evaluated using porcine and human aortic roots as control. A 13% solution (w/v) of PVA (Dupont Canada Inc: Elvanol HV 99.0–99.8% hydrolysis. (MW 1,000,000) was cast on a Petri dish and thermally cycled, one cycle comprising −70° C. for 11 to 13 hours and ambient temperature (25° C.) for 11 to 13 hours. The PVA was cut into rectangular strips (20 mm×10 mm×5 mm) for tensile testing using Material Test System (MTS). The MTS testing was performed in distilled water at 37° C. The cross-head speeds used were 0.3 mm/s, 3 mm/s, and 30 mm/s (physiological strain rate).

Figure 5:
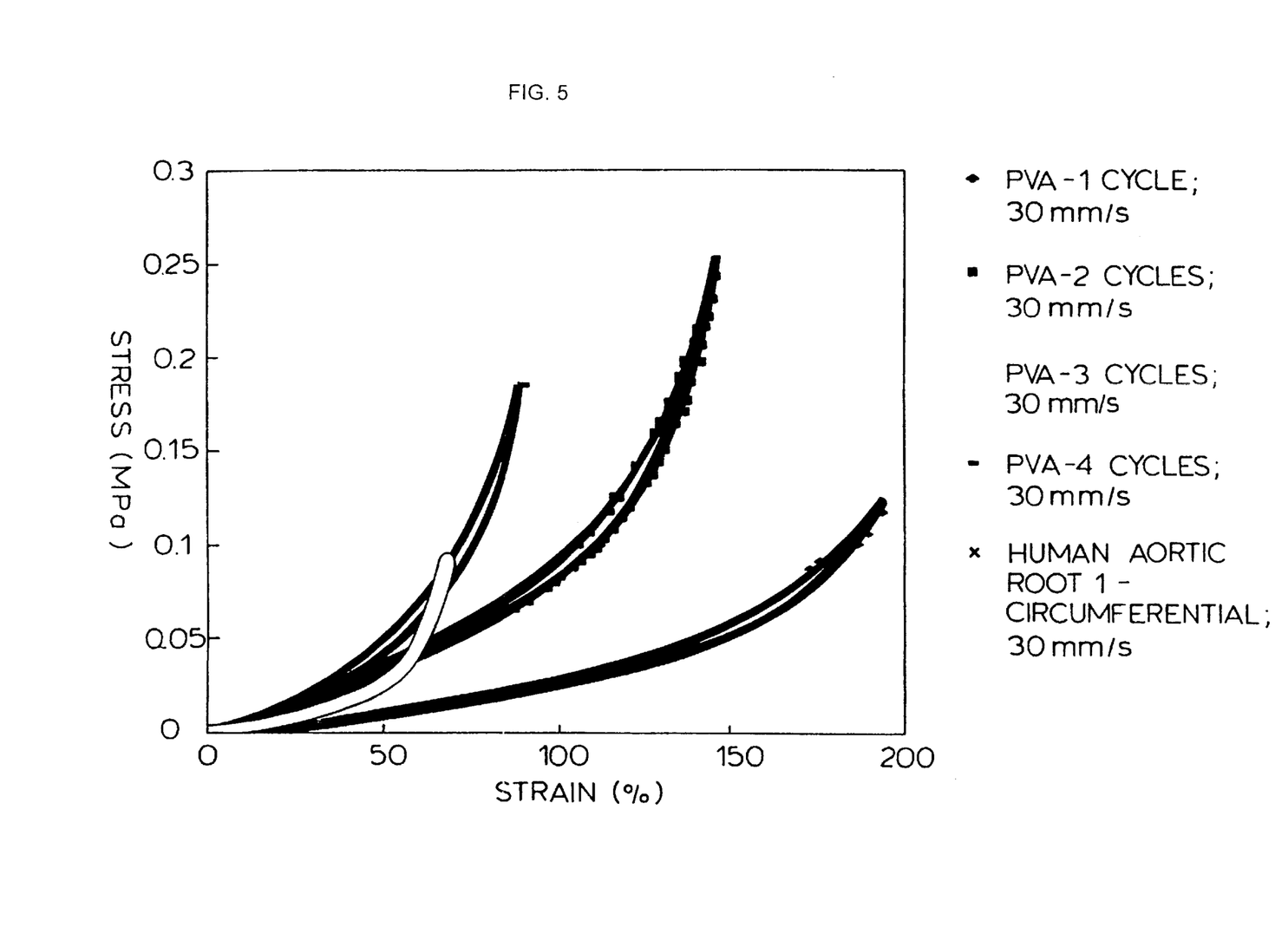
FIG. 5 shows stress-strain curves for PVA after various numbers of freeze-thaw cycles and for aortic root (white curve).

The stress-strain curves (FIG. 5) illustrate a progressive increase in elastic moduli with increasing number of thermal cycles. The mechanical properties of the human aorta were closely matched by the PVA exposed to 4 thermal cycles.

Tables 2 and 3 show further results and indicate the closeness of the PVA properties to those of human aorta.

The thermal cycling causes an entropic re-ordering of the molecular chains during thawing. This re-ordering causes physical cross-links to occur between the carbon chains. Consequently, this process increases the elastic moduli of the polymer. Repeated thermal cycling (up to 4 cycles) continually enhances the mechanical properties.

Example 4

A polyethylene stent of a design similar to the Medtronic stent was designed by computer aided design and was machined from polyethylene, using computer controlled machining techniques described in "Machining of poly (hema) stent" (1992), Evans, D., $4^{th}$ year Engineering Thesis, University of Western Ontario. This stent was then used as a model to form a solution casting mould.

Figure 2:
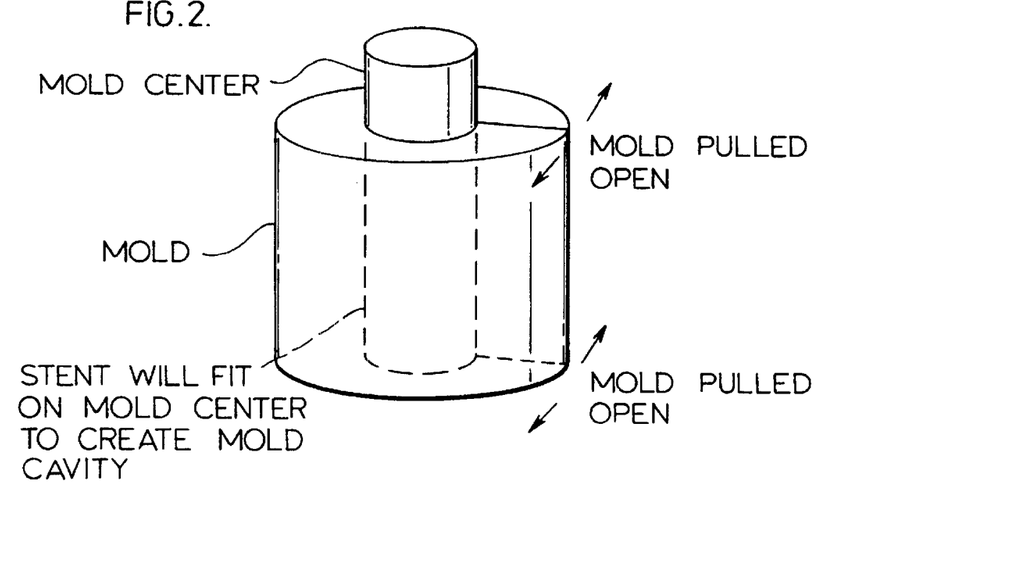
FIG. 2 is a diagram of a mould design for solution casting of a hydrogel stent.

The mold design used consisted of a central rod, used to create the inside diameter of the stent, while the mold surrounded this central rod, as seen in FIG. 2.

This also shows how the mold is expected to be opened after casting is completed. There would be a single vertical cut made into the mold material, used to remove a stent that has been cast. In order to cast PVA or PolyHEMA in solution, there must be an appropriate place for the solution to enter the mold cavity. The mold should also have a means to allow air in the mold cavity to escape to the atmosphere as it is displaced by incoming polymer solution. Mold filling was designed to have a drilled cavity in the bottom section of the mold center. Three 1/32" holes 120° apart further up the mold center would be used to allow a solution to travel from the cavity in the mold center to the mold cavity itself. The mold is positioned so that these holes are located at the lower stent ring, directly under the peaks of the three valve posts seen in FIG. 2.

Dow offers a range of mold making packages which have different mechanical properties, thereby creating molds for specific applications. All of the mold packages consist of a liquid silicone rubber base and a catalyst used to cure the silicone base. The catalyst uses addition polymerization to carry out this curing process. Table 1 illustrates some of the important properties of the Silastic mold making packages and should be used to help one decide on an appropriate mold material.

TABLE 1

Properties of Dow Corning Silastic mold making materials.

|  | E | J | L | M | S | T-2 |
|---|---|---|---|---|---|---|
| Specific Gravity | 1.12 | 1.28 | 1.27 | 1.29 | 1.12 | 1.12 |
| Viscosity (poise) | 500 | 900 | 1000 | 900 | 128 | 550 |
| Durometer Hardness (points) | 37 | 56 | 34 | 59 | 26 | 42 |
| Tensile Strength (psi) | 800 | 900 | 550 | 650 | 1000 | 800 |
| Elongation (%) | 350 | 250 | 350 | 250 | 900 | 300 |
| Tear Strength (ppi) | 110 | 90 | 50 | 90 | 140 | 120 |
| Shrinkage after 24 h @25° C. | NIL | NIL | NIL | NIL | NIL | NIL |
| Shrinkage after 7 days @25° C. | 0.1 | 0.1 | 0.1 | 0.1 | 0.1 | 0.1 |

It was decided that the Silastic E-type mold material should be used for the solution casting operation. A relatively low viscosity during mold making is important as the base-catalyst mixture will be poured to create the mold. A low viscosity will allow the mixture to confirm to the stent geometry more easily than a mixture with a high relative viscosity. Other very important properties are the elongation as well as tensile and tear strengths. These mechanical properties must be relatively high, because the mold will have only one vertical cut through its volume, and as will be seen shortly, it must be flexible enough to allow the cast stent to be extracted from the mold, yet strong enough to withstand the high degree of elongation anticipated during stent extraction. Perhaps one of the most important properties of all the Silastic molding materials is that none of them undergo any appreciable dimensional changes during the mold making procedure. This is important because one would like to alleviate as many parameters, such as accounting for mold shrinkage.

Figure 3:
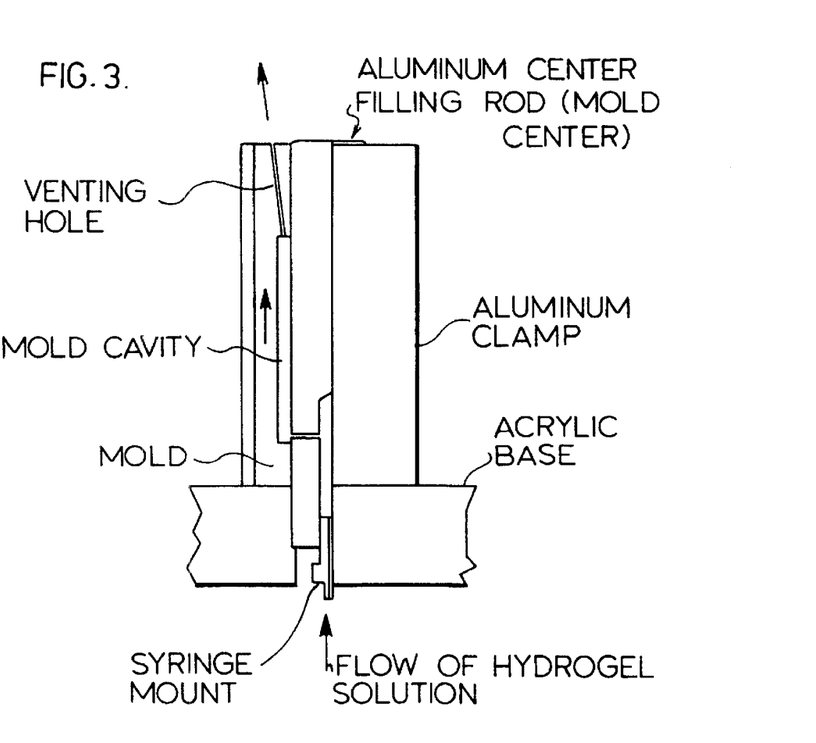
FIG. 3 is a sectioned view of a mold of the type shown in FIG. 2.

Two parts of the casting fixture that will be discussed later, were used to create the mold, this being the mold center (aluminum) and short piece of aluminum tubing. FIG. 3 illustrates how the mold was made. The first step was to apply the paraffin wax to the stent in order to increase its size and thereby increase the size of the heart valve stent to be cast. The stent used to create the mold had to be vertically positioned so that the mold filling holes, as previously described, are located in the middle of the lower stent ring, and directly under the peaks of the valve posts. Paraffin wax was melted at 75° C., and the mold center, with attached stent, was then dipped into the wax and removed. After allowing the wax to solidify, a scalpel was used to trim wax from the stent perimeter, and between stent features such as the area surrounded by the valve post and upper ring. This procedure was repeated three times in order to create a wax layer approximately 0.5 mm thick. The mold center and stent was then placed through a slide fit hole in a ⅝" thick plate of acrylic that respectively sat on another place of acrylic without a hole. This was done because the mold center prior to casting is press fit ⅝" into an acrylic base. Thus to offset this, the acrylic plate with a slide fit hole (with respect to the outside diameter of the mold center) was used. A 2½" long section of 1¾" I.D. tubing was then centered about the mold center axis, on the upper acrylic surface. This was used to contain the mold material as it cures. In order to create the necessary cavity venting holes, ³⁄₆₄" monofilament was attached to the peak of each valve post at one end, and to the top rim of the aluminum tube at the other. The mold material was mixed in a 10:1 ratio of silicone rubber compound to catalyst. After thorough mixing, the mold material was poured into the aluminum tube to a height of approximately 2⅛". The entire mold making unit was put under a vacuum of 80 psi for 50 minutes. This was done to help remove any air bubbles trapped in the mold material. The mold making unit was then allowed to cure for 48 hours. The aluminum tube was cut twice lengthwise (180° C. apart) to extract the mold. A scalpel was used to carefully make one cut lengthwise through the mold material, in order to extract the stent used to create the mold, and to provide a means for mold opening and closing as previously described.

Figure 4:
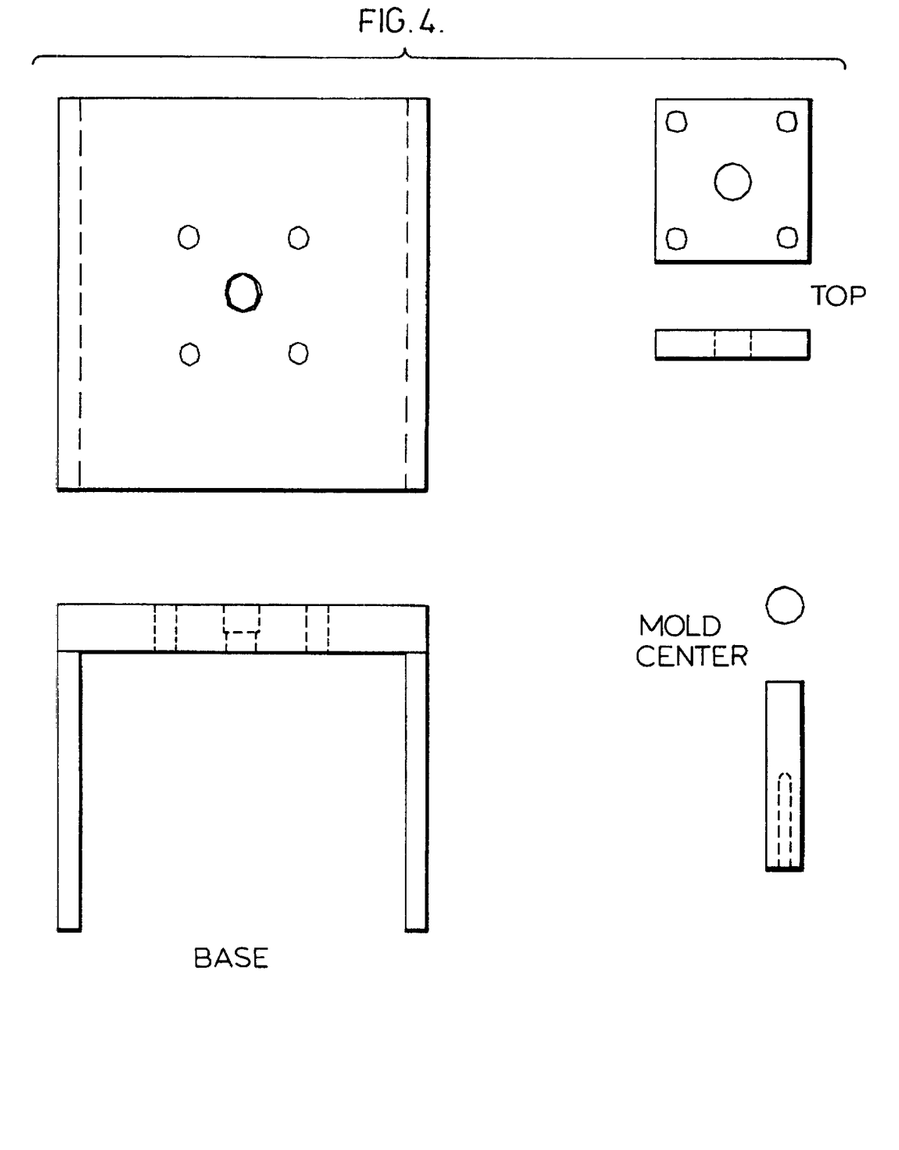
FIG. 4 is a schematic representation of the components of the mold fixture.

FIG. 4 gives a schematic representation of the components and dimensions of the mold fixture.

The base is composed of two ½" thick acrylic plates used as legs for the rest of the fixture. These legs have then been bonded to a 1" thick acrylic place used to mount all the components involved with casting. Acrylic was chosen for these parts because it is relatively inexpensive and for the ease with which acrylic can be machined. A counter bore was put into the center of the 1" thick plate, in order to press fit the mold center into a permanent position. The four holes surrounding the central counter bore are used to fit fine threaded rod, which will be used to tighten the top down onto the sides of the aluminum tubing during casting. The top is also made of acrylic, and has a sliding fit hole at its center to accommodate the mold center during clamping. The mold center is made of aluminum. Aluminum was chosen as we require a surface that will not react with any solvent that it may come into contact with. The bottom of the mold center was drilled and taped to accept a standard syringe fixture. The three ¹⁄₃₂" holes that will allow dissolved hydrogel to enter the mold cavity were then drilled. After the mold center was used to make the mold, it was press fit into the counter bore in the acrylic base.

15 g of PVA powder was dissolved in 100 ml distilled water in a water bath maintained at 70° C.

A 10 mL syringe was used to inject the solution into the mold. The syringe was attached to the syringe attachment in the bottom of the mold center. Pressure was then applied to the syringe plunger to fill the mold center cavity, the mold cavity, and finally to have the solution escape through the mold venting holes. Some of the hydrogel solution was allowed to collect at the top of the mold after exiting through the venting holes, in order to be sure that the mold had been completely filled. FIG. 3 illustrates the flow of dissolved hydrogel through the entire mold.

With the mold filled, the entire casting apparatus was placed in a freezer at −80° C. for 15 hours, at which time the apparatus was then removed from the freezer to slowly warm to room temperature (~20° C.). This was done because PVA must undergo a minimum of one freeze/thaw cycle in order to become rigid enough to be removed from the mold.

The PVA stent was fully hydrated in water for 24 hours and was then subjected to three further freeze/thaw cycles, to improve its strength.

TABLE 1

Mechanical Properties of poly(hema) vs. Polypropylene

| Material | Elastic Modulus (Gpa) | Strain at UTS (%) | Yield Stress (Mpa) | Relaxation Rate (%) |
|---|---|---|---|---|
| Polypropylene | 0.6–25 | ~30 | — | — |
| Poly(hema) | ~0.1 | ~60 | 20–30 | 6.8 |

TABLE 2

Modulus Values

| Material | Modulus (MPa) |
|---|---|
| Porcine Aorta | 5.17 |
| Human Aorta | 0.61 |
| PVA - 4 Thermal Cycles | 0.61 |

TABLE 3

Relaxation Rates

| Material | Relaxation Slopes (kPa/s) |
|---|---|
| Porcine Aorta | 7.69 |
| Human Aorta | 5.75 |
| PVA - 4 Thermal Cycles | 6.92 |

We claim:

1. A bioprosthetic valve stent fabricated from a hydrogel, wherein the hydrogel, when hydrated, has
   (a) a strain value at ultimate tensile stress (UTS) greater than the maximum strain occurring in a human aortic root under physiological conditions;
   (b) an elastic modulus similar to that of the aortic root; and
   (c) a relaxation rate similar to that of the aortic root.

2. The valve stent of claim 1 wherein the hydrogel has
   (a) a strain at UTS of at least 20%;
   (b) an elastic modulus in the range of about 0.01 to about 10 Mpa; and
   (c) a relaxation rate in the range of about 3 to about 9 kPa/sec.

3. The stent of claim 2 wherein the hydrogel is a polyvinyl alcohol hydrogel.

4. The stent of claim 4 wherein the stent is an aortic valve stent.

5. The stent of claim 1 wherein the hydrogel is selected from the group consisting of poly(vinyl alcohol), polyacrylamide, poly(N-vinylpyrolidone), poly(hydroxyethyl methacrylate), poly(ethylene oxide), poly(ethylene glycol), poly(ethylene glycol) monomethyl ether, cellulose, poly(acrylate), polymethacrylate, poly(methylacrylate), poly(methyl methacrylate) and poly(lactic acid).

6. A bioprosthetic heart valve comprising
a) a stent in accordance with claim 1,
(b) leaflet valve means having three generally triangular leaflets defining respective cusps which are adapted to open and close during heart systole and diastole respectively; and
(c) means for attaching the leaflet valve means to the stent.

7. The valve of claim 6 wherein the leaflet valve means is selected from the group consisting of glutaraldehyde-pretreated bovine pericardial tissue or glutaraldehyde-pretreated porcine aortic valve cusps.

8. A method of fabricating a bioprosthetic valve stent comprising the steps of:
(a) preparing a mold cavity corresponding in shape to the stent to be fabricated;
(b) filling said mold cavity with a solution of a selected hydrogel;
(c) allowing the hydrogel to solidify; and
(d) directly after step (c) removing the solidified hydrogel from the mold cavity and hydrating the solidified hydrogel for a suitable period of time.

9. The method of claim 8 wherein the selected hydrogel is PVA and wherein step (c) comprises subjecting the filled mold cavity to at least one freeze-thaw temperature cycle and wherein the method further comprises step (e) subjecting the hydrated hydrogel to at least three freeze-thaw temperature cycles.

10. The method of claim 9 wherein each freeze-thaw temperature cycle employs a freezing temperature in the range of about −70° C. to −30° C. and a thaw temperature in the range of about 15° C. to 30° C.

11. An aortic valve stent fabricated from a hydrogel by a process in accordance with claim 9.

12. The method of claim 8 wherein the selected hydrogel is PVA and wherein step (c) comprises subjecting the filled mold cavity to at least four freeze-thaw temperature cycles.

13. The method of claim 12 wherein each freeze-thaw temperature cycle employs a freezing temperature in the range of about −70° C. to −30° C. and a thaw temperature in the range of about 15° C. to 30° C.

14. An aortic valve stent fabricated from a hydrogel by a process in accordance with claim 12.

15. A bioprosthetic valve stent fabricated from a hydrogel by a process in accordance with claim 8.

\* \* \* \* \*

UNITED STATES PATENT AND TRADEMARK OFFICE
CERTIFICATE OF CORRECTION

PATENT NO. : 6,458,156 B1
DATED : October 1, 2002
INVENTOR(S) : Wan-Kei Wan et al.

It is certified that error appears in the above-identified patent and that said Letters Patent is hereby corrected as shown below:

<u>Column 8,</u>
Line 58, change "The stent of claim 4" to -- The stent of claim 3 --.

Signed and Sealed this

Twenty-fifth Day of February, 2003

JAMES E. ROGAN
*Director of the United States Patent and Trademark Office*